(12) United States Patent
Trumbull et al.

(10) Patent No.: US 9,044,291 B2
(45) Date of Patent: Jun. 2, 2015

(54) JAW POWERED ELECTRIC GENERATOR

(75) Inventors: Thomas R. Trumbull, Los Gatos, CA (US); Timothy P. Johnston, Los Gatos, CA (US)

(73) Assignee: Plantronics, Inc., Santa Cruz, CA (US)

( * ) Notice: Subject to any disclaimer, the term of this patent is extended or adjusted under 35 U.S.C. 154(b) by 550 days.

(21) Appl. No.: 13/467,665

(22) Filed: May 9, 2012

(65) Prior Publication Data
US 2013/0300345 A1    Nov. 14, 2013

(51) Int. Cl.
*H02N 2/18*      (2006.01)
*A61C 13/271*    (2006.01)
*A61C 5/08*      (2006.01)
*F03G 5/06*      (2006.01)
*A63B 71/08*     (2006.01)

(52) U.S. Cl.
CPC ... *A61C 5/08* (2013.01); *F03G 5/06* (2013.01); *H02N 2/18* (2013.01); *A61C 13/26* (2013.01); *A63B 71/085* (2013.01)

(58) Field of Classification Search
CPC ............ A61C 8/00; A61C 5/08; A61C 13/26; F03G 5/06; H02N 2/18; H02J 7/32
See application file for complete search history.

(56) References Cited

U.S. PATENT DOCUMENTS

| | | | |
|---|---|---|---|
| 1,986,955 A | 1/1935 | Bedell | |
| 5,033,999 A | 7/1991 | Mersky | |
| 6,115,477 A | 9/2000 | Filo et al. | |
| 7,269,266 B2 | 9/2007 | Anjanappa et al. | |
| 7,844,070 B2 | 11/2010 | Abolfathi | |
| 2004/0202344 A1 | 10/2004 | Anjanappa et al. | |
| 2009/0208031 A1 | 8/2009 | Abolfathi | |
| 2009/0226020 A1 | 9/2009 | Abolfathi et al. | |
| 2010/0194333 A1* | 8/2010 | Kassayan et al. | 320/108 |
| 2010/0290647 A1 | 11/2010 | Abolfathi et al. | |
| 2012/0212178 A1* | 8/2012 | Kim | 320/108 |

* cited by examiner

*Primary Examiner* — Vuthe Siek
*Assistant Examiner* — Aric Lin

(57) ABSTRACT

An electric generator powered by the opening and closing of a user's jaw. In one embodiment, a portion of an electric generator is mechanically stressed by a user's teeth when the user opens or closes his jaw. The mechanical stress is converted to electric energy and may be stored in a battery or power an electric device. In another embodiment, a magnet is passed through a coil when the user opens or closes his jaw to generate electric energy.

26 Claims, 11 Drawing Sheets

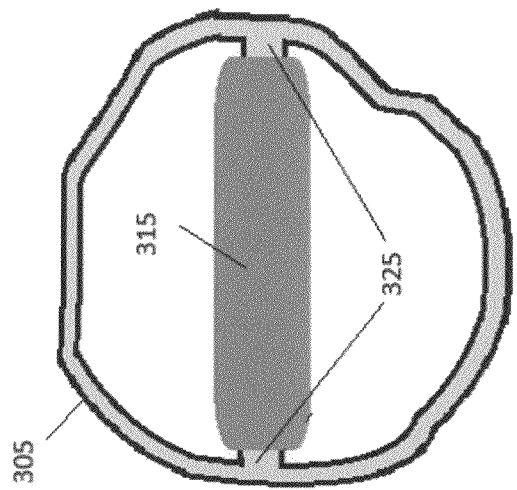
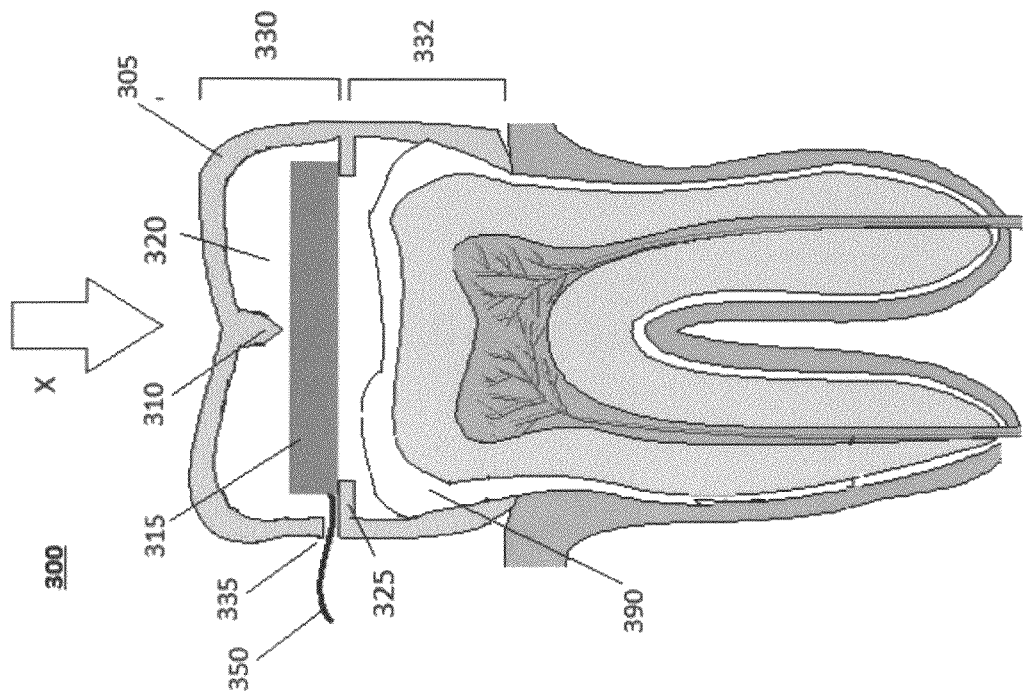
FIGURE 3B
FIGURE 3A

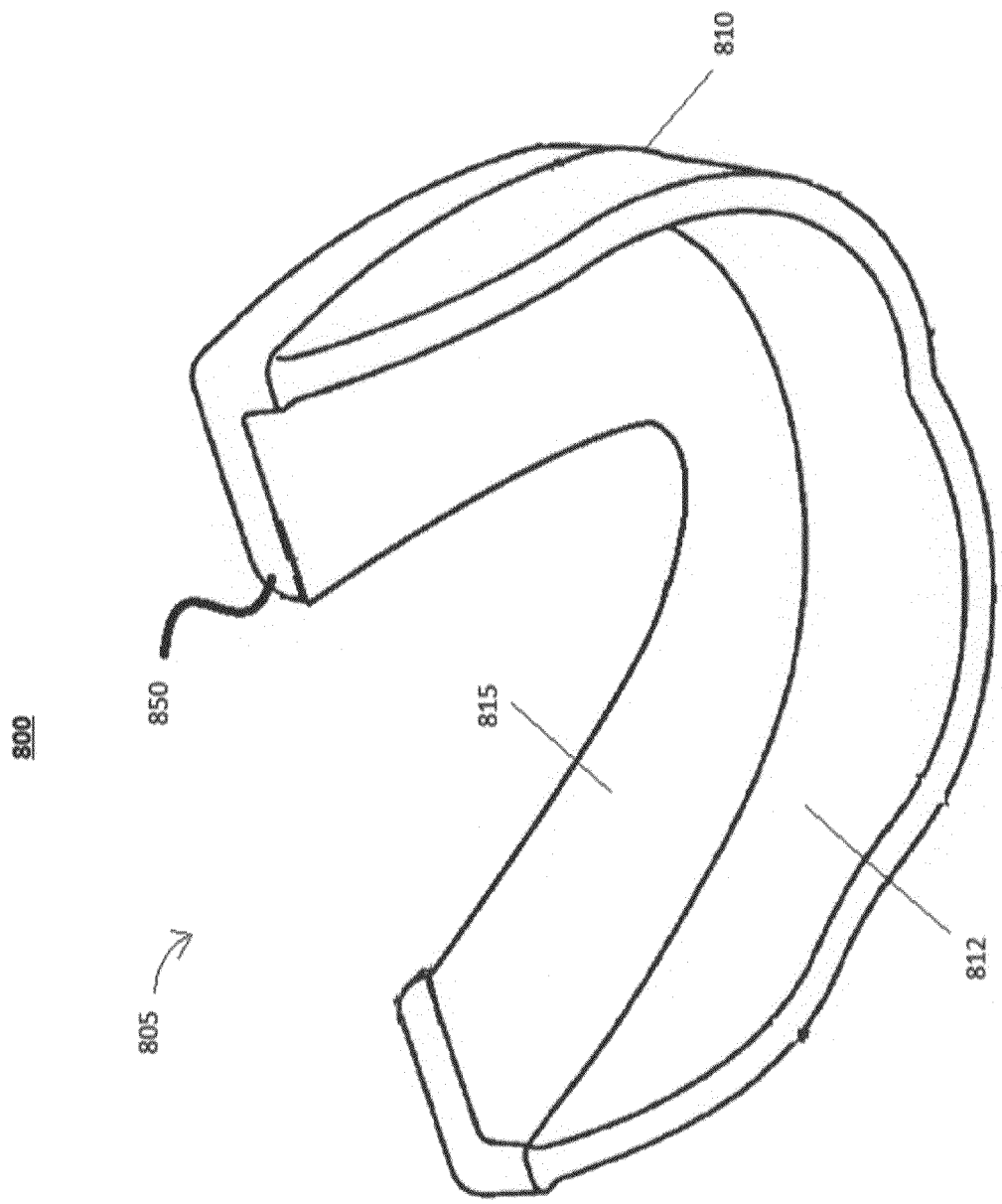

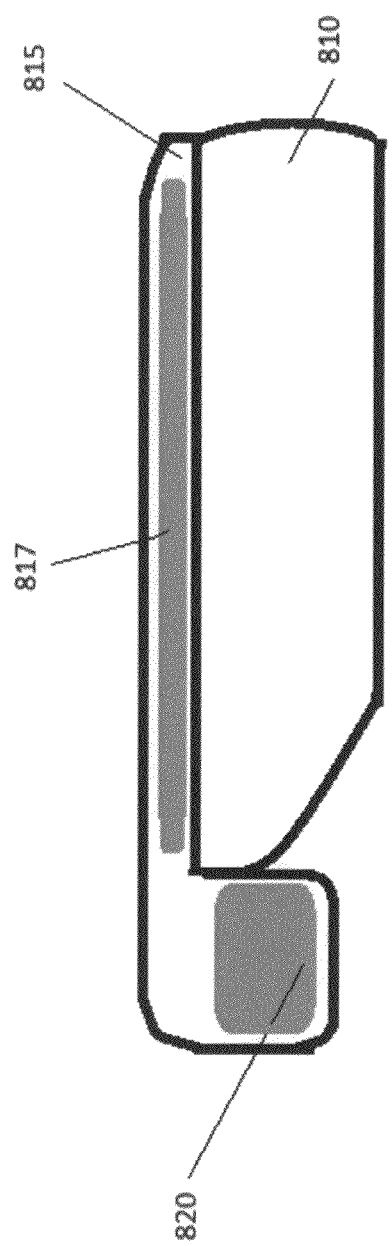

JAW POWERED ELECTRIC GENERATOR

BACKGROUND OF THE INVENTION

As electronics devices become increasingly powerful and smaller, powering these devices has become a significant concern. It may be troublesome to find compatible power sources when a user is frequently mobile and devices often require multiple recharges per day. Electronic device users typically address this issue by carrying multiple pre-charged batteries or multiple electric adapters, such as a car adapter or Universal Serial Bus adapter. This solution is cumbersome and inconvenient to the user.

SUMMARY OF THE INVENTION

According to one aspect of the invention, an apparatus comprises a first portion configured to be fixed with respect to a user's upper jaw or the user's lower jaw, a second portion configured to be movable with respect to the first portion and an electric generator adapted to generate electric energy from relative motion between the first portion and the second portion.

In one embodiment, the electric generator is located within the mouth of the user. A portion of the electric generator may be retained in a cavity defined by a portion of the first portion and a portion of the second portion. The relative motion between the first portion and second portion may be initiated responsive to relative motion between the user's upper jaw and the user's lower jaw. For example, the user may move his upper and lower jaw while talking or chewing.

The electric generator may comprise a piezoelectric transducer which may comprise a piezoelectric film and/or piezoelectric ceramic. The piezoelectric transducer is mechanically stressed by the relative motion between the first portion and the second portion. In one embodiment, the piezoelectric transducer is mechanically stressed responsive to a user's tooth applying a force to the second portion. In another embodiment, the electric generator comprises a coil and magnet. The magnetic is passed through a coil to generate electric energy responsive to a user's tooth applying a force to the second portion.

The apparatus may further comprise a circuit, such as a rectifier, for converting the electric energy to direct current. A battery may be configured to store the electric energy. The battery may be removably coupled to the user, such as coupling the battery to a user's tooth. After the battery is charged, the battery may be decoupled from the user's tooth and placed in an electronic device. Alternatively, the apparatus may provide electric energy directly to an electronic device.

The apparatus may be implemented in an artificial tooth or fake tooth such as a pontic. In this embodiment, the artificial tooth may comprise a first portion configured to be fixed with respect to a user's upper jaw or the user's lower jaw, a second portion configured to be movable with respect to the first portion and an electric generator adapted to generate electric energy from relative motion between the first portion and the second portion.

In another embodiment an apparatus comprises a cap coupled to a portion of a tooth and an electric generator adapted to generate electric energy from relative motion between the cap and the portion of the tooth. The tooth may be physically coupled to a user's upper jaw or the user's lower jaw, and the relative motion between the cap and the portion of the tooth may be initiated responsive to relative motion between the user's upper jaw and the user's lower jaw.

The electric generator may comprise a piezoelectric transducer having a piezoelectric electric film and/or piezoelectric ceramic. The piezoelectric transducer may be mechanically stressed by the relative motion between the cap and the portion of the tooth. The mechanical stress may be responsive to a user's tooth applying a force to the cap. Alternatively the electronic generator may comprise a coil and magnet. A portion of the electric generator may be retained in a cavity defined by the portion of the tooth and the cap.

The apparatus may further comprise a circuit, such as a rectifier, for converting the electric energy to direct current. A battery may be coupled to the circuit to receive and store electric energy. The battery and/or circuit may be removably coupled to the user. The battery and/or circuit may be stored within a cavity defined by the cap and portion of the tooth or stored elsewhere in the user's mouth such as on the surface of adjacent teeth. After the battery is charged, the battery may be decoupled from the user and placed in an electronic device. Alternatively, the apparatus may provide electric energy directly to an electronic device.

Another embodiment of the present invention comprises a method for generating electric energy wherein generating the electric energy comprises mechanically stressing a portion of an electric generator. Mechanically stressing the portion of the electric generator comprises at least one of opening a human jaw, and closing the human jaw. The method may further comprise storing the electric energy in a battery.

BRIEF DESCRIPTION OF THE DRAWINGS

FIG. 3A is a cross-sectional side view of a jaw generator on a tooth;

FIG. 3B is a cross-sectional top view of a jaw generator on a tooth;

FIG. 8A is a drawing of the jaw generator in accordance with another embodiment of the present invention;

FIG. 8C is a drawing of the jaw generator in accordance with another embodiment of the present invention;

DETAILED DESCRIPTION OF THE DRAWINGS

The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

Furthermore, those skilled in the art will appreciate that the reference to a tooth as used herein is intended to encompass any type of tooth, including but not limited to molars, premolars, third molars, wisdom teeth, incisors, canines and artificial teeth such as dental bridges and dental crowns.

Figure 1:
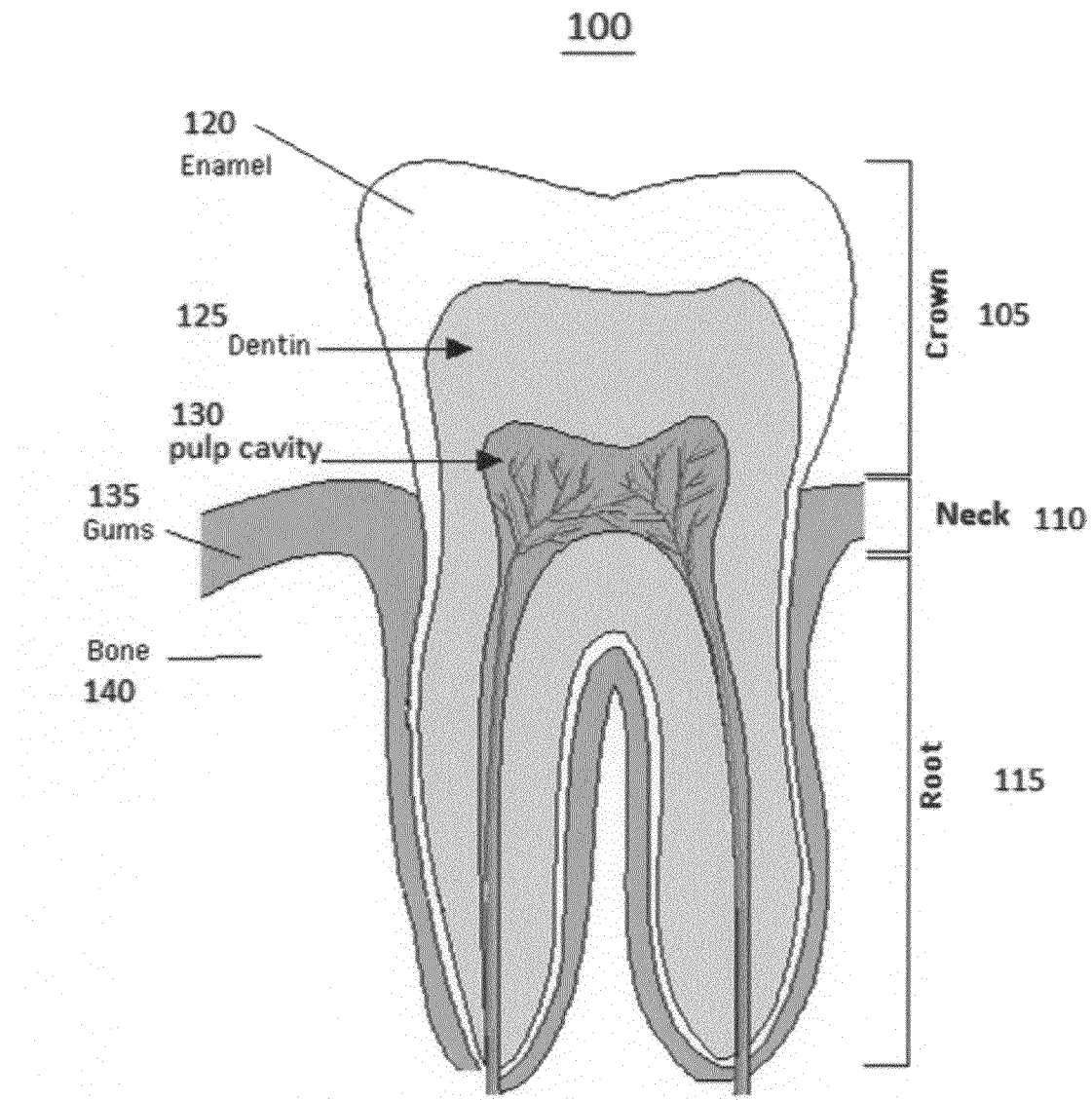
FIG. 1 is a diagram of the anatomy of a tooth.

Referring to FIG. 1, shown is a diagram of a molar tooth 100. The tooth 100 comprises a crown 105, neck 110, root 115, enamel 120, dentin 125, and pulp cavity 130. The base of the tooth 100 is surrounded by gums 135 and a portion of the jaw bone 140.

Conventionally, the crown 105 is considered the visible portion of the tooth above the neck 110. The crown 105 is generally completely covered by enamel 120. Below the layer of enamel 120 is a layer of dentin 125. Below layer of dentin 125 is the pulp cavity 130. The pulp cavity 130 may contain blood vessels and nerves that run through the pulp of the tooth. The root 115 is conventionally considered the portion of the tooth below the neck 110. The root 115 assists in anchoring the tooth 100 into the jaw bone 140.

Figure 2:
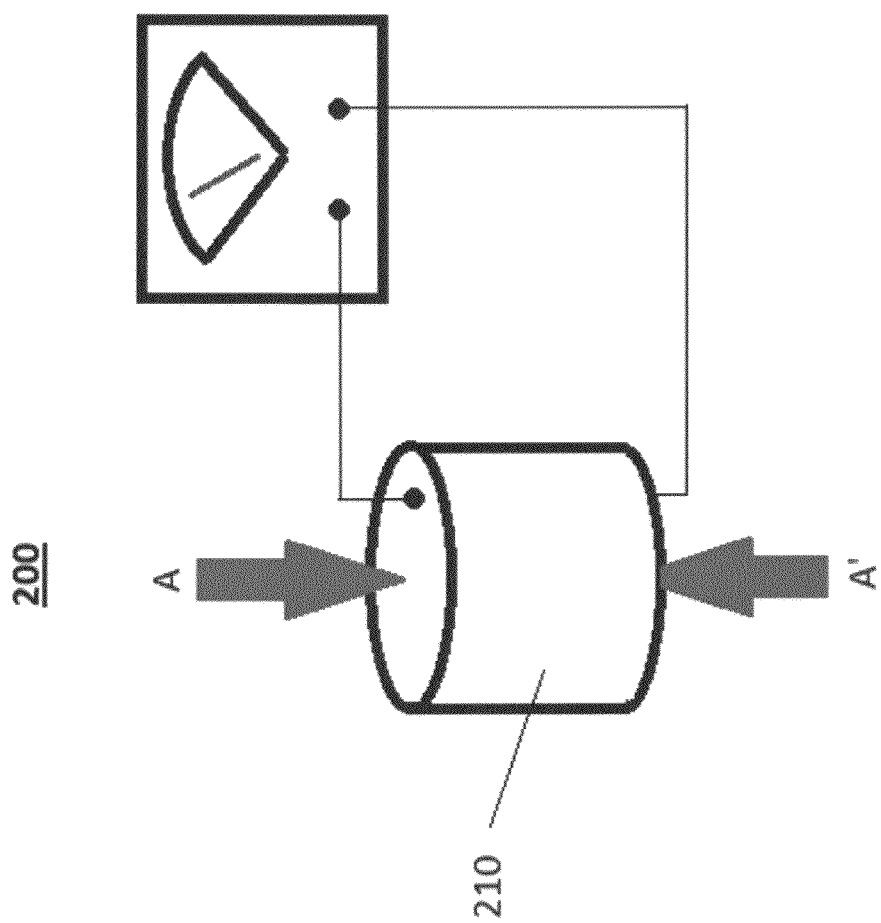
FIG. 2 illustrates a conventional piezoelectric generator.

Referring to FIG. 2, shown is an illustration of an electric generator in the form of a conventional piezoelectric transducer 200. The piezoelectric transducer 200 comprises a piezoelectric element 210. The piezoelectric element 210 converts electric energy into mechanical vibrations (transmit mode) and mechanical vibrations into electric energy (receive mode). The piezoelectric element 210 may comprise materials known in the art including but not limited to ceramics, crystals, and magnetostrictive materials. In receive mode, the piezoelectric element 210 generates electric energy when deformed (i.e. in response to applied mechanical stress or force). In one embodiment, the piezoelectric element 210 generates electric energy when a force at AA' is applied and mechanical stress occurs.

Referring to FIG. 3 shown is a cap 305, piezoelectric element 315 and a tooth 390 according to one embodiment 300. The cap 305 comprises at least one top protrusion 310, a top portion 330, a base portion 332, an aperture 335 and support protrusions 325.

The cap 305 is coupled to the tooth 390. Similar to a dental crown, the cap 305 may be shaped to the dimensions of a tooth's crown and configured to cover the tooth 390. When coupled, the cap 305 can fully encase the visible portion of the tooth 390 that lies at and above the gum line, but this is not required. The cap 305 comprises an open end at the base portion 332 for receiving the tooth 390. The cap 305 may be removably coupled to the tooth 390. Alternatively, the cap 305 may be permanently coupled to the tooth 390 by an adhesive such as glue or cement.

The cap 305 may be made from one or more materials suitable for dentistry such as ceramics, resins, porcelain, alloys and metals. When coupled, the tooth 390 and cap 305 define a cavity 320 wherein the piezoelectric element 315 is disposed. The piezoelectric element 315 may be a piezoelectric ceramic or piezoelectric film and may take various forms such as a strip, disk or block. Electric wires 350 connect the piezoelectric element 315 to a circuit or energy storage device (not shown) by passing through the aperture 335 in cap 305.

The top portion 330 of the cap 305 is configured to deform toward the piezoelectric element 315 when a force X is applied to the upper surface of the cap 305 and uncompress to its original shape when a force is no longer applied. The elasticity of the top portion 330 may be achieved by choice of material, thickness and/or form design. The top portion 330 may be made from a different material than the base portion 332. The base portion 332 is fixed with respect to the tooth 390 and user's jaw; it is configured to keep the cap 305 rigidly coupled to the tooth while the top portion 330 is compressed.

The top protrusion 310 extends from the inner surface of the top portion 330 toward the piezoelectric element 315 and is configured to apply a force to the piezoelectric element 315 when force X is applied. When the top portion 330 is uncompressed, the top protrusion 310 is sufficiently positioned to not apply a force to the piezoelectric element 315.

The piezoelectric element 315 is coupled to one or more support protrusions 325. The support protrusions 325 are configured to support the piezoelectric element 315 in the cavity 320 and provide lateral support. The support protrusions 325 may be made from the same material and/or mold as the cap 305. Referring to FIG. 3A and FIG. 3B, support protrusions 325 extend a finite length from the inner surface of the cap 305 to support the outer edge of the piezoelectric element 315. It should now be understood that the piezoelectric element 315 is suspended in cavity 320 and can be mechanically stressed by the top protrusion 310 when the top portion 330 is compressed. In an alternative embodiment, support protrusions 325 may comprise one piece to support the entire body of the piezoelectric element 315.

Figure 4:
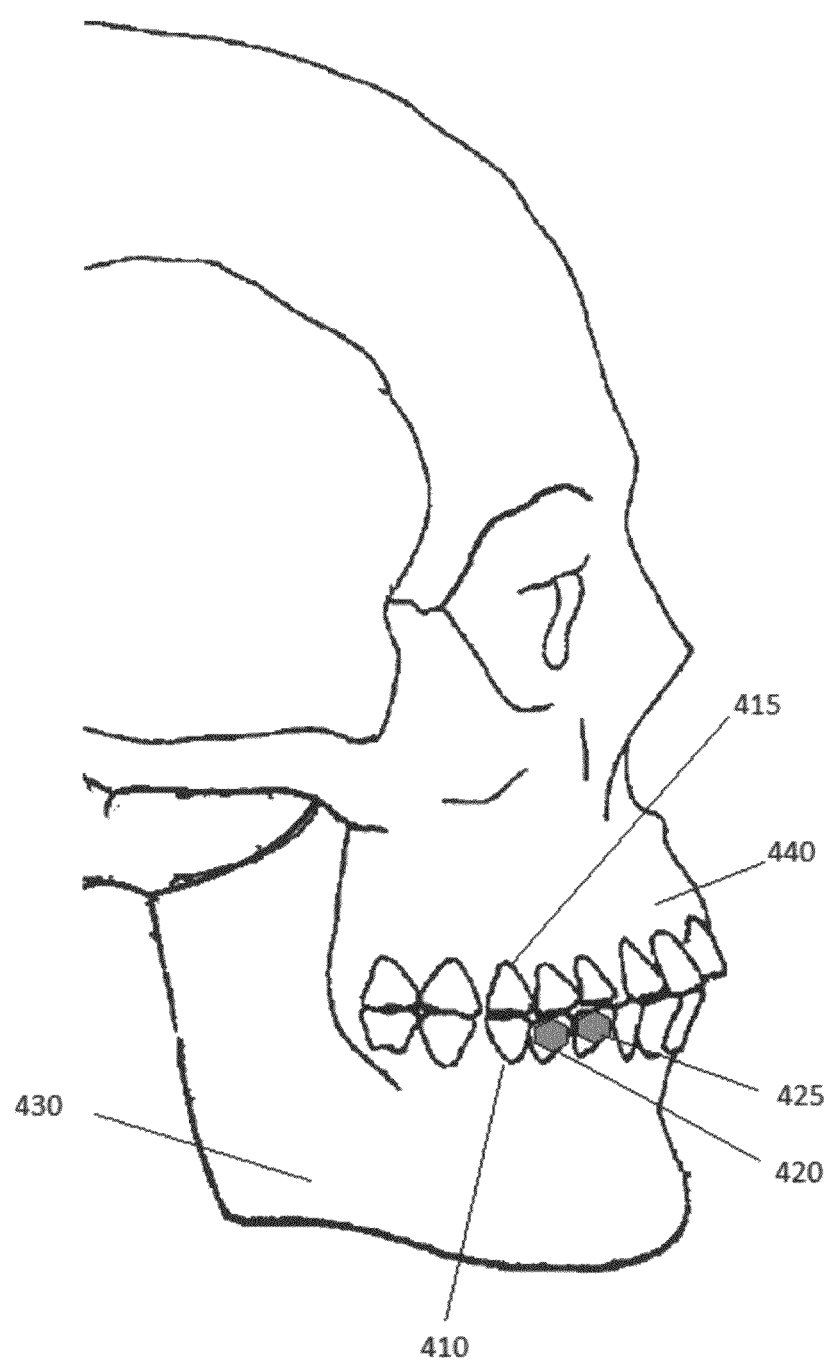
FIG. 4 is a cross-section side view of the jaw generator of FIG. 3 placed in a user's mouth.

The operation of the embodiment 300 can now be understood. Turning to FIG. 4, shown is the cap 305 of FIG. 3 placed in the mouth of a user on tooth 410 at the lower jaw 430. When selecting a tooth to couple the cap 305 onto, it is preferred to select a tooth that has a corresponding tooth on the opposing jaw such that the opposing tooth applies adequate force to the cap 305 when the user's jaw is closed. In some cases, one or more corresponding teeth on the opposite jaw may apply force to the selected tooth when the user's jaw is closed. Tooth 410 has a corresponding tooth 415 located on the upper jaw 440.

Figure 5A:
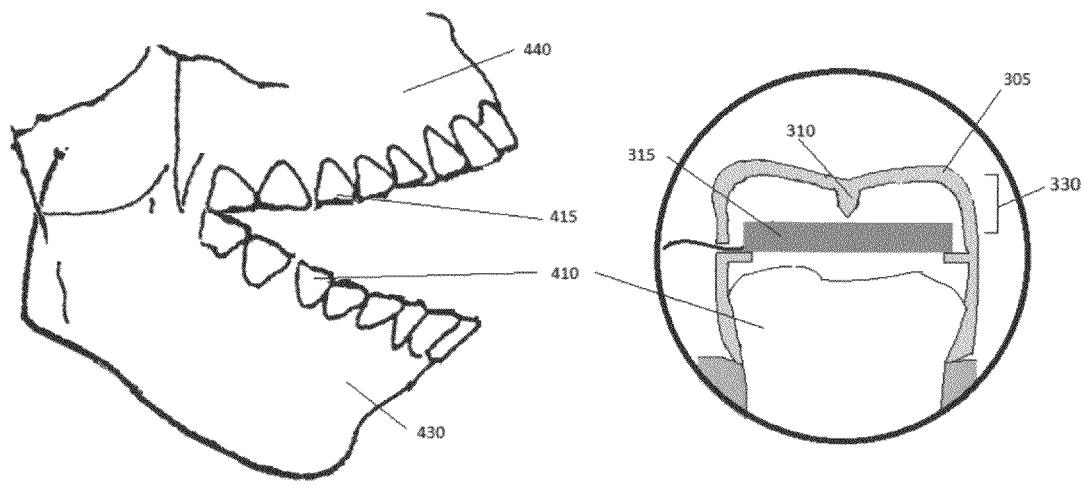
FIG. 5A and FIG. 5B is an illustration of the jaw generator of FIG. 3 in use.
Figure 5B:
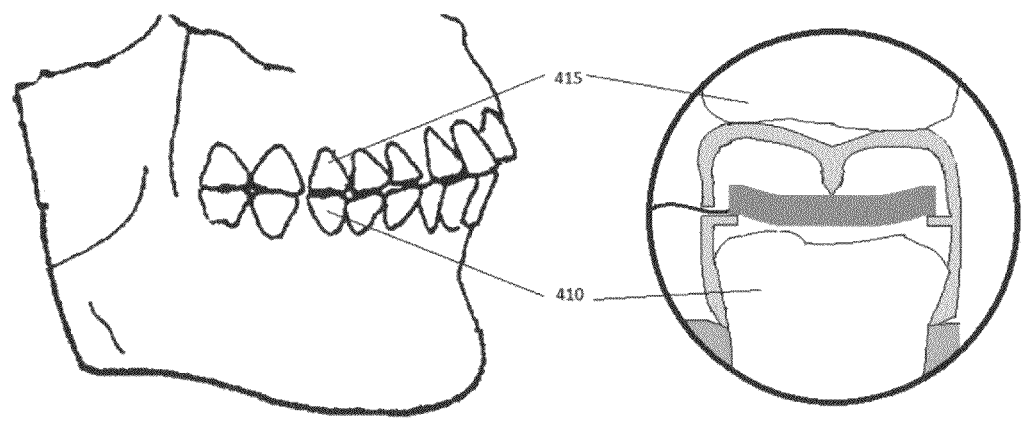

Referring to FIG. 5A, shown is the cap 305 and tooth 410 when the user's jaw is in an open position. In the open position, no force or insufficient force is applied to the cap 305 and the piezoelectric element 315 is not mechanically stressed. When the user's jaw transitions to a closed position as seen in FIG. 5B, the tooth 415 applies a force to the cap 305 at the top portion 330. The top portion 330 is compressed toward the piezoelectric element 315 and the top extension 310 applies a force to the piezoelectric element 315. The force applied to the piezoelectric element 315 causes mechanical stress (e.g. deformity), and in turn the piezoelectric element 315 produces electric energy. When the user's jaw transitions to back to an open position (FIG. 5A), the top portion 330 returns to an uncompressed state and the top protrusion 310 no longer applies a force to the piezoelectric element 315. In turn the piezoelectric element 315 also returns to an unstressed state and produces electric energy. When the user's jaw repetitively transitions to and from an open and closed position, the piezoelectric element 315 generates electric energy in the form of alternating electric current.

The alternating current may be transported by electric wires 350 to an electric circuit 420 such as a rectifier to convert the alternative current to direct current. The electric circuit 420 may be electrically coupled to an energy storage device 425 (shown in FIG. 4) such as a battery or capacitor, for storing the direct current. The electric circuit 420 and energy storage device 425 may be located on the surface of adjacent teeth. In one embodiment they are electrically coupled by wires. Alternatively, they may be electrically coupled by conductive contacts placed between adjacent teeth.

Figure 6A:
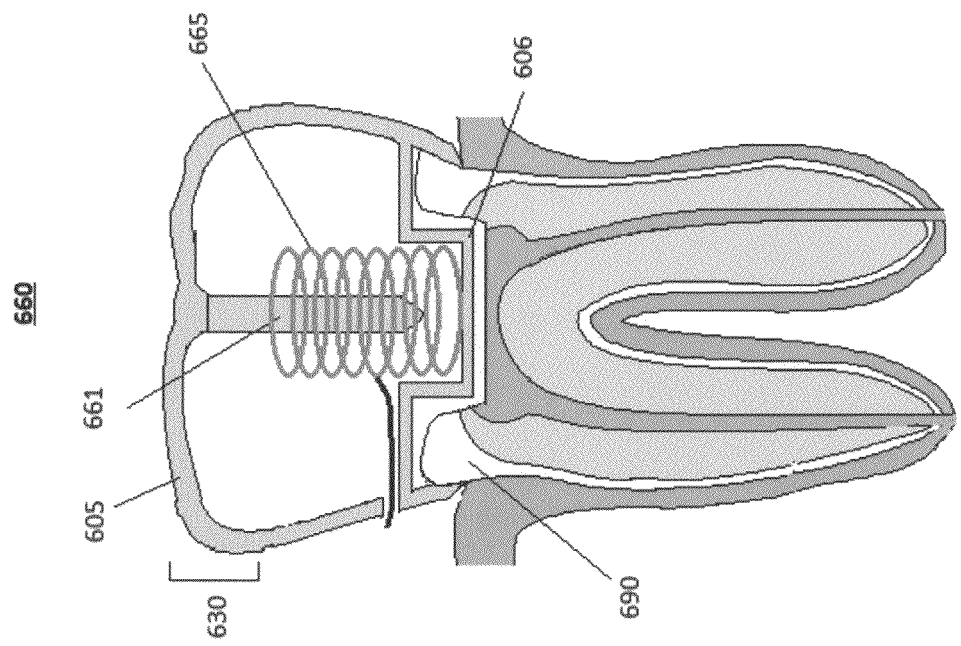
FIG. 6A is a drawing of the jaw generator in accordance with another embodiment of the present invention.

Referring to FIG. 6A, shown is an alternative embodiment 600 in which the piezoelectric element 615 takes the form of a cantilever. In this embodiment, the piezoelectric element 615 is anchored by a support protrusion 625 at one end; the top protrusion 610 may be disposed near the opposite end of the piezoelectric element 615. Furthermore, the top protrusion 610 extends from the inner surface of the top portion 630 toward the piezoelectric element 615. If the user has had a root canal procedure, a portion of the root of the tooth 690 is removed and the pulp cavity within the center of the tooth can be made available to house an electric circuit 640 and energy storage device 645. The electric circuit 640 and energy storage device 645 may be coupled directly to the inner surface of the pulp cavity or be supported by a substrate 606. Electric wires 650 connect the electric generator directly to an electronic device (not shown) by passing through an aperture 635 in cap 605.

Figure 6B:
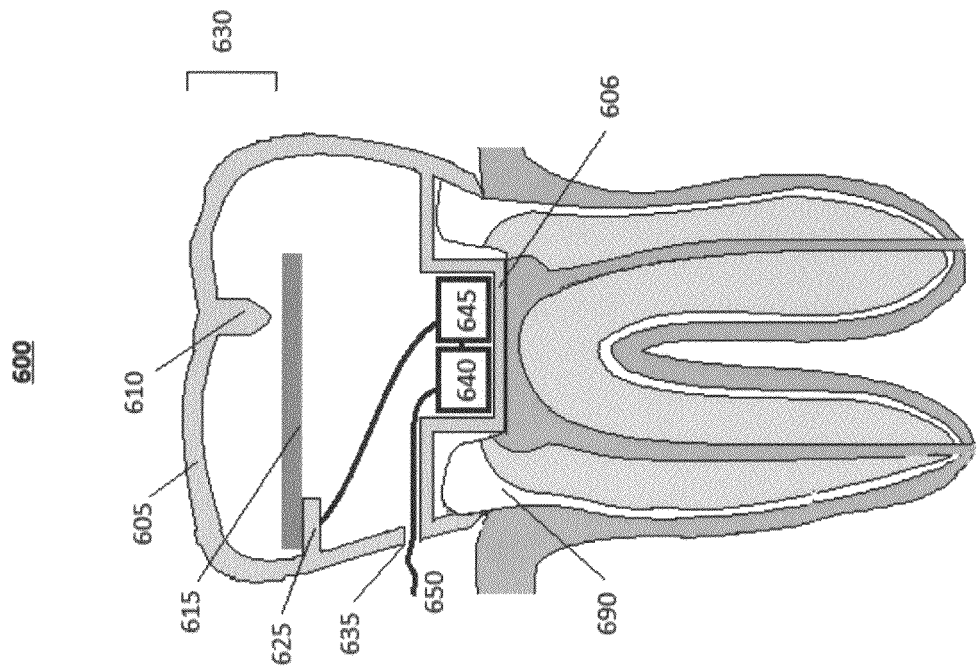
FIG. 6B is a drawing of the jaw generator in accordance with another embodiment of the present invention.

Referring to FIG. 6B, shown is an alternative embodiment 660 in which the electric generator takes the form of a magnet 661 and coil 665. The magnet 660 is coupled to the inner surface of the top portion and extends downward. The coil 665 may be fixed to a substrate 606. In this embodiment, a magnet 660 is passed through the center of the coil 665 when a sufficient force is applied to the top portion 630 of the cap 605. The movement of the magnet 661 through the coil 665 induces an electric current as the user opens and closes his jaw. Alternatively, the position of the magnet 661 and coil 665 may be reversed such that the magnet 661 is fixed to the substrate 606 and the coil 665 is coupled to the inner surface of the top portion 630.

Figure 7:
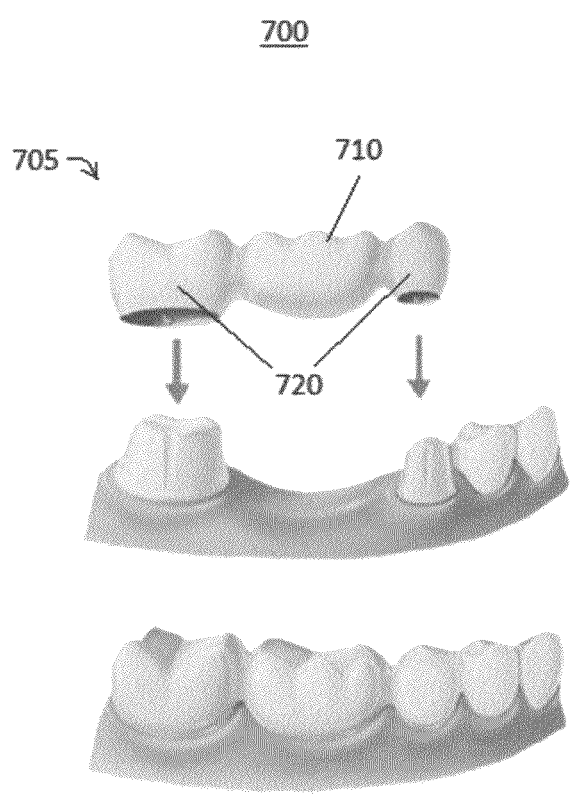
FIG. 7 is a drawing of the jaw generator in accordance with another embodiment of the present invention.

Referring to FIG. 7, shown is an alternative embodiment 700 wherein the jaw-powered electric generator takes the form of dental bridge 705. The dental bridge 705 comprises a pontic 710 and crowns 720. In this embodiment, an electric generator similar to those of embodiments 300 and 600 is implemented in the pontic 710. An array of electric generators may be arranged if the crowns 720 also include electric generators similar to those of embodiments 300 or 600.

Referring to FIG. 8A, shown is another embodiment diagram wherein the jaw-powered electric generator takes the form of a retainer 805. The retainer 805 comprises a base 810 and a lip portion 815. The retainer 805 is shaped to conform to the lower portion of the user's mouth much like a traditional mouth guard or dental retainer. It will be appreciated that the retainer 805 may alternatively be configured to conform to the upper portion of the user's mouth (e.g., upper jaw).

The base 810 is U-shaped and surrounds the user's lower teeth when the retainer 805 is placed in the user's mouth. The base 810 has an inner surface 812 which comes into contact with a portion of the user's teeth and a portion of the lower gums. The base 810 may comprise materials known in the art including but not limited to polymers, plastics and silicone. The lip portion 815 extends from one end of the base portion 810 toward the center of the mouth such that a portion of the lip portion 815 covers the top surface of the user's teeth. A portion of the lip portion 815 is a made from a compressible piezoelectric material 817 (shown in FIG. 8C). The piezoelectric material 817 of the lip portion 815 may be encased in the same material as base 810. An electric wire 850 connects the lip portion 815 to a circuit or energy storage device (not shown).

Figure 8B:
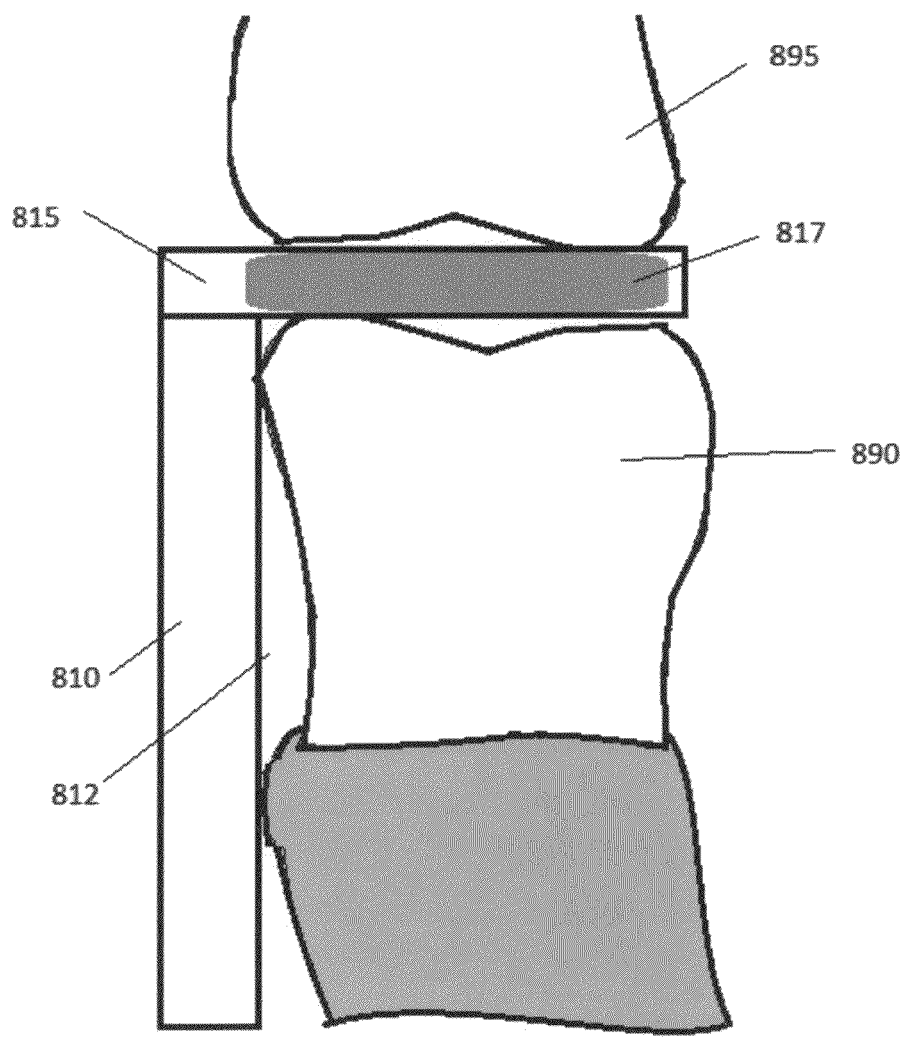
FIG. 8B is a cross sectional view of the jaw generator of FIG. 8A placed in a user's mouth.

FIG. 8B shows a cross-sectional view of a portion of the retainer 805 when placed in the user's mouth. The operation of the device can now be understood. Similar to the embodiments 300, 600, 660 and 700 the lip portion 815 is not mechanically stressed when the jaw is in an open or rest position. In the rest position, no force or insufficient force is applied to the lip portion 815. When the user's jaw transitions to a closed position the tooth 890 and opposing tooth 895 compresses/stresses the lip portion 815 and consequently compresses/stresses piezoelectric material 817. This phenomenon occurs across the entire array of teeth. When the user repetitively transitions to and from an open and closed position, the piezoelectric material 817 generates electric energy in the form of alternating current.

The base 810 and lip portion 815 may cover all or some of the user's teeth. The base 810 may be configured to be lingual, buccal, distal or a combination thereof. Furthermore, the portions of the lip portion 815 may have various thicknesses and dimensions to account for the various types of teeth surfaces.

FIG. 8C shows an alternative embodiment wherein an end portion 820 may extend toward the back of the mouth. The end portion 820 may extend from lip portion 815 such that a portion of the end portion 820 covers a portion of the user's gum, such as an operculum. The end portion 820 comprises a compressible piezoelectric material such as a piezoelectric ceramic. When the user's jaw transitions to an open and closed position the end portion 820 is stressed and unstressed by the user's gums to generate electric energy.

Figure 9:
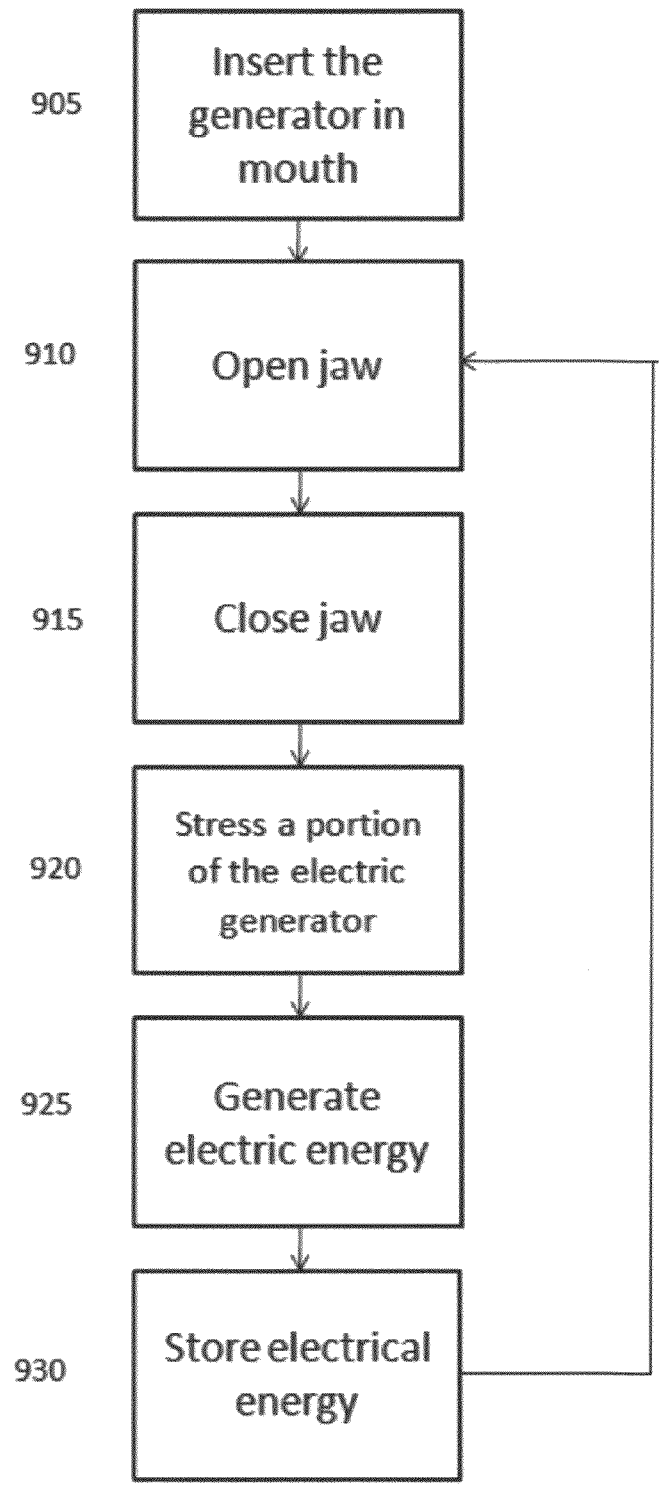
FIG. 9 is a flow chart diagram of the jaw generator in operation.

FIG. 9 shows a flow chart demonstrating the jaw powered generator in use. At step 905, generator is placed in the user's mouth. The generator rests in the user's mouth until the user opens his jaw at 910. Next, the user closes his jaw 915. Opening 910 and closing 915 may be invoked by typical actions of the mouth such as talking, chewing, and biting. One benefit of the invention is the user generates power throughout the day using the natural use of his mouth without conscious effort. The user may also purposely invoke steps 910 and 915 with the intent to generate electric energy. Also the sequence of steps of opening 910 and closing 915 the jaw may be reverse although not explicitly shown in FIG. 9. At step 920 a portion of the electric generator is mechanically stressed or deformed. In the case of the embodiments of 300 and 600 a portion of a cap is compressed to deform a piezoelectric element 315. In the case of embodiment 660 a portion of a cap is compressed to move a magnet through a coil. In the case of embodiment 660 a portion of a cap is compressed to move a magnet 661 through a coil 665. In the case of embodiment 800 opposing teeth compress a lip portion 815. At step 930 the electric energy is storage in an energy storage device such as a battery 645. The electric energy may be sent to an appropriate electric circuit 640 such as a rectifier prior to the storage device to convert the electric energy to direct current. Next, the method returns to step 910 and repeats when the user open and closes his jaw.

What is claimed is:

1. An apparatus comprising:
   a first portion configured to be fixed with respect to a user's upper jaw or the user's lower jaw;
   a second portion configured to be movable with respect to the first portion; and
   an electric generator adapted to generate electric energy from relative motion between the first portion and the second portion, wherein the electric generator comprises a piezoelectric transducer.

2. The apparatus of claim 1, wherein the relative motion between the first portion and second portion is initiated responsive to relative motion between the user's upper jaw and the user's lower jaw.

3. The apparatus of claim 1, wherein the piezoelectric transducer is mechanically stressed by the relative motion between the first portion and the second portion.

4. The apparatus of claim 1, wherein the piezoelectric transducer is mechanically stressed responsive to a user's tooth applying a force to the second portion.

5. The apparatus of claim 1, wherein the piezoelectric transducer comprises a piezoelectric film.

6. The apparatus of claim 1, wherein the piezoelectric transducer comprises a piezoelectric ceramic.

7. The apparatus of claim 1, further comprising a circuit for converting the electric energy to direct current.

8. The apparatus of claim 1, further comprising a battery configured to store the electric energy.

9. The apparatus of claim 8, wherein the battery is removably coupled to the user.

10. The apparatus of claim 1, wherein the electric generator is located within the mouth of the user.

11. An artificial tooth comprising the apparatus of claim 1.

12. An apparatus comprising:
    a first portion configured to be fixed with respect to a user's upper jaw or the user's lower jaw;
    a second portion configured to be movable with respect to the first portion; and
    an electric generator adapted to generate electric energy from relative motion between the first portion and the second portion, wherein at least a portion of the electric generator is retained in a cavity defined by a portion of the first portion and a portion of the second portion.

13. An apparatus comprising: a cap coupled to a portion of a tooth; and an electric generator adapted to generate electric energy from relative motion between the cap and the portion of the tooth.

14. The apparatus of claim 13, wherein the electric generator comprises a piezoelectric transducer.

15. The apparatus of claim 14, wherein the piezoelectric transducer is mechanically stressed by the relative motion between the cap and the portion of the tooth.

16. The apparatus of claim 14, wherein the piezoelectric transducer is mechanically stressed responsive to a user's tooth applying a force to the cap.

17. The apparatus of claim 14, wherein the piezoelectric transducer comprises a piezoelectric film.

18. The apparatus of claim 14, wherein the piezoelectric transducer comprises a piezoelectric ceramic.

19. The apparatus of claim 13, wherein the electric generator comprises a coil and magnet.

20. The apparatus of claim 13, wherein the tooth is physically coupled to a user's upper jaw or the user's lower jaw, and wherein the relative motion between the cap and the portion of the tooth is initiated responsive to relative motion between the user's upper jaw and the user's lower jaw.

21. The apparatus of claim 13, further comprising a circuit for converting the electric energy to direct current.

22. The apparatus of claim 13, further comprising a battery configured to store the electric energy.

23. The apparatus of claim 13, wherein the battery is removably coupled to the user.

24. The apparatus of claim 13, wherein at least a portion of the electric generator is retained in a cavity defined by the portion of the tooth and the cap.

25. A method comprising:
    generating electric energy; wherein generating the electric energy comprises mechanically stressing a portion of an electric generator;
    wherein mechanically stressing the portion of the electric generator comprises at least one of opening a human jaw, and closing the human jaw.

26. The method of claim 25, further comprising storing the electric energy in a battery.

* * * * *